United States Patent [19]

Rothgery

[11] 4,204,857
[45] May 27, 1980

[54] 5-XANTHOGENATO-3-TRIHALOMETHYL-1,2,4-THIADIAZOLES AND THEIR USE AS HERBICIDES

[75] Inventor: Eugene F. Rothgery, North Branford, Conn.

[73] Assignee: Olin Corporation, New Haven, Conn.

[21] Appl. No.: 6,041

[22] Filed: Jan. 24, 1979

[51] Int. Cl.² .................. A02N 9/12; A01N 21/02; C07D 285/05
[52] U.S. Cl. .................................. 71/73; 71/90; 548/129
[58] Field of Search ............. 260/302 SD; 71/90, 73

[56] References Cited

U.S. PATENT DOCUMENTS

| Re. 29,439 | 10/1977 | Parsons | 260/302 SD |
|---|---|---|---|
| 3,260,725 | 7/1966 | Schroeder | 260/302 D |
| 3,573,317 | 3/1971 | Smith | 260/302 D |
| 3,691,183 | 9/1972 | Thaler | 260/302 SD |
| 3,821,236 | 6/1974 | Ripple | 260/302 SD |
| 3,884,929 | 5/1975 | Smith | 260/302 SD |
| 3,888,869 | 6/1975 | Pews et al. | 260/302 SD |

Primary Examiner—Alton D. Rollins
Attorney, Agent, or Firm—William A. Simons; Thomas P. O'Day

[57] ABSTRACT

Disclosed are selected 5-xanthogenato-trihalomethyl-1,2,4-thiadiazole compounds of the formula:

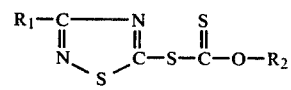

wherein $R_1$ is a $CCl_3$ or $CF_3$ group and $R_2$ is a lower alkyl group having 1 to 4 carbon atoms. These compounds are shown to have post-emergence herbicidal activity.

4 Claims, No Drawings

5-XANTHOGENATO-3-TRIHALOMETHYL-1,2,4-THIADIAZOLES AND THEIR USE AS HERBICIDES

BACKGROUND OF THE INVENTION

1. Field of the Invention

This invention relates to selected 5-xantho genato-3-trihalomethyl-1,2,4-thiadiazole compounds and their use as herbicides.

2. Description of the Prior Art

Various 3,5-substituted-1,2,4-thiadiazole compounds have been known to possess different types of pesticidal activities such as fungicidal, herbicidal, insecticidal, nematocidal and the like. For example, U.S. Pat. No. 3,260,725, which issued to Hansjuergen A. Schroeder on July 12, 1966, discloses the use of 3-trichloromethyl-5-ethylthio or 5-isobutylthio-1,2,4-thiadiazole compounds as soil fungicides. Furthermore, this patent suggests that these prior art compounds may have other pesticidal activities (see Column 1, lines 49–57 of the patent).

BRIEF SUMMARY OF THE INVENTION

Accordingly, the present invention is directed to, as compositions of matter, selected 5-xanthogenato-3-3-trihalomethyl-1,2,4-thiadiazole compounds of the formula:

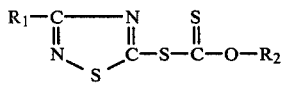
(I)

wherein $R_1$ is $CCl_3$ or $CF_3$ group and $R_2$ is a lower alkyl group having 1 to 4 carbon atoms. The present invention also covers the use of these compounds as post-emergence herbicides.

DETAILED DESCRIPTION

The selected 5-xanthogenato-3-trihalomethyl compounds of the present invention may be prepared by reacting the corresponding 5-chloro-3-trihalomethyl-1,2,4-thiadiazole with the desired alkali metal (lower alkyl) xanthate salt. This general reaction is illustrated below in Equation (A) by the reaction of 5-chloro-3-trichloromethyl-1,2,4-thiadiazole with potassium ethyl xanthate.

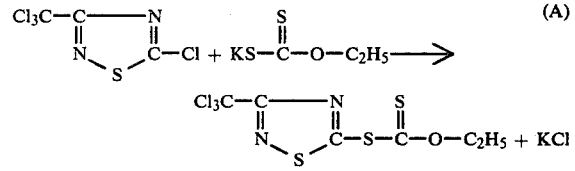
(A)

Suitable 5-chloro-3-trihalomethyl-1,2,4-thiadiazole reactants for this type of reaction include 5-chloro-3-trichloromethyl-1,2,4-thiadiazole and 5-chloro-3-trifluoromethyl-1,2,4-thiadiazole. The former compound is described in the above-mentioned U.S. Pat. No. 3,260,725, and may be prepared by reacting trichloroacetamidine hydrochloride with trichloromethane sulfenyl chloride in the presence of a base. The latter compound is described in H. A. Schroeder's *Journal Organic Chemistry*, 27, 2589 (1962) and is prepared by the sidechain fluorination of 5-chloro-3-trichloromethyl-1,2,4-thiadiazole with Swart's fluorination mixture consisting of antimony trifluoride, antimony trichloride and chlorine.

Suitable alkali metal (lower alkyl) xanthate reactants include above-mentioned potassium ethyl xanthate, potassium or sodium methyl xanthate, potassium or sodium propyl xanthate, and potassium or sodium isopropyl xanthate salts. Potassium ethyl xanthate is commercially available. All of these noted xanthate salts are conveniently made from potassium or sodium hydroxide, carbon disulfide and appropriate alcohol. See Rao, *Xanthates and Related Compounds*, Marcel Dekker, Inc., New York, 1971, for more detailed description of their preparation.

Any conventional reaction conditions may be employed in the synthesis of the present compounds and the present invention is not intended to be limited to any particular reaction conditions. Advantageously and preferably, the reaction is carried out using approximately equal molar quantities of the two reactants in the presence of a suitable inert hydrocarbon solvent such as alcohols and the like. Ethanol is a preferred solvent, but other inert solvents may be used. The reaction temperatures and time will both depend upon many reaction parameters including the exact reactants being employed, but in most situations, reaction temperatures from about 0° C. to about 130° C. and reaction times from about 1 hour to about 30 hours are preferred. The desired product may be recovered from the reaction mixture by any conventional means, for example, distillation or simply by cooling the reaction mixture and removing the precipitated product by filtration. Finally, it should be noted that while the reaction illustrated by Equation (A) is a preferred method of preparing compounds of the present invention, other synthesis methods may also be employed.

In accordance with the present invention, it has been found that compounds of Formula (I), above, may be used for defoliation or for desiccation of the green parts of plants. They are, in particular, suitable singly, or in mixtures thereof, for the control of weeds. As contemplated herein, the terms "weeds" is meant to include not only weeds in the narrow sense, but also in the broad sense, whereby to cover all plants and vegetation considered undesirable for the particular purposes in question. Whether the active compounds according to the present invention act as total or selective herbicides depends essentially on the amount applied, as the artisan will appreciate.

Specifically, in practicing the process of the present invention, undesirable plant and vegetation are contacted with a herbicidally effective amount of the above-mentioned compounds. It is to be understood that the term "herbicidally effective amount" as used in the specification and claims herein is intended to include any amount that will kill or control said undesirable plants and vegetation when either employed by itself (i.e., in full concentration) or in sufficient concentration with a carrier or other substance. Of course, this amount may be constantly changing because of the possible variations in many parameters. Some of these may include: the number and type of plants to be controlled or killed; the type of loci or media to which the present compounds can be applied (e.g., weeds within crop areas, fence lines); degree of effectiveness required; and type of carrier, if any. The step of contacting may be accomplished by applying the present active compounds to the undesirable plants themselves or to the immediate locus or ground surrounding said plants.

For most situations, the application of the compounds of the present invention in amounts from about 0.1 pound per acre to about 10 pounds per acre will be sufficient for selective or total herbicidal effect.

The above-mentioned compounds of the present invention may be formulated and applied to any conventional methods that include using the compounds alone or with a carrier or other substances which may enhance the effectiveness of the chemical or facilitate handling. Moreover, the activity of the present compounds may be broadened by the addition thereto of other known biocides.

Specific methods of formulating and applying these active compounds include applying them in the form of dusts, dust or emulsion concentrates, wettable powders, and concentrates, granulates, dispersions, sprays, solutions and the like.

The dusts and dust concentrate are usually prepared by simply grinding together the active compounds of the present invention with a finely divided inert diluent such as walnut flour, diatomaceous earth, fuller's earth, attaclay, talc or kaolin. Dusts generally contain from about 1% to about 15% by weight of active compound and dust concentrates usually contain from about 16% to about 75% by weight active compound. In practice, dust concentrates are usually admixed with more inert diluent at the site of use to form dusts before being applied to undesirable plant foliage.

Wettable powders are generally prepared in the same manner as dust concentrates, but usually about 1% to 10% by weight of a dispersing agent, for example, an alkali metal lignosulfonate and about 1% to 10% of a surfactant, such as a non-ionic surfactant, are incorporated in the formulation. For most applications, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray application.

It is possible to formulate granulates whereby these active compounds are dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, one of the above-mentioned active compounds, of more than one active compound, is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that such herbicide formulations, the ingredients which may make up such formulations other than the active compounds and the dosages, and means of applying these formulations may include all known and conventional substances, amounts and means, respectively, that are suitable for obtaining the desired herbicidal result. Therefore, such process parameters are not critical to the present invention.

Besides the above-described herbicidal effect, compounds of the present invention have shown foliar fungicidal activity.

The following examples further illustrate the present invention. All parts and percentages employed therein are by weight unless otherwise indicated.

EXAMPLE 1

Preparation of 5-(Ethylxanthogenato)-3-Trichloromethyl-1,2,4-Thiadiazole 8.5 grams (0.05 mole) of potassium ethylxanthate and 12 grams (0.05 mole) of 5-chloro-3-trichloromethyl-1,2,4-thiadiazole were stirred in 300 milliliters of ethanol for 30 minutes at 35° C. The resulting white solids were filtered off and the filtrate evaporated under vacuum to give a yellow solid. Recrystallization from ethyl ether gave two crops of product totaling 15 grams, melting point 84°-87° C. Elemental and infra-red analyses confirmed the product to be 5-(ethylxanthogenato)-3-trichloromethyl-1,2,4-thiadiazole.

Herbicide Screen

The active material made in Example 1 was tested for activity as effective herbicides by the following method.

A uniform aqueous dispersion of the chemical was made by dissolving the chemical in a solution of acetone containing a nonionic surfactant in a concentration of 500 ppm. The resulting solution was diluted with water (1:9) to obtain a mixture of 10% acetone, 0.05% surfactant, 0.208% test candidate made by Example 1, and the balance water; 50 milliliters of this solution applied to a flat of 144 square inches corresponds to 10 lb/acre. If further dilutions were required for testing at lower concentrations, water was added to this stock solution and the surfactant maintained at 50 ppm.

The aqueous solutions containing each chemical were applied to flats seeded with representative monocotyledonous and dicotyledonous plants. The test chemical was applied to one such flat immediately after it was seeded (pre-emergence screening) and to the other flat after the first true plant leaves had developed (post-emergence screening). Response was rated 12 to 21 days after treatment on a scale of 0 to 10, where 0 represents no injury and 10 represents complete kill. Tables I and II, below, show the results of this testing.

The crops and weeds used for the determination of activity were: Foxtail Millet (*Setaria italica*), Japanese Millet (*Echinochloa crusgalli*), Crabgrass (*Digitaria sanguinalis*), Wild Oats (*Avena fatua*), Morning Glory (*Ipomoea purpurea*), Mustard (*Brassica nigra*), Pigweed (*Amaranthus retroflexus*), Sesbania (*Sesbania exaltata*), Velvet Leaf (*Abutilon theophrasti*), Soybean (*Glycine max*), Cotton (*Gossypium hirsutum*), and Tomato (*Lycopersicon esculentum*).

TABLE I

| GENERAL HERBICIDE ACTIVITY AT 10 LBS./ACRE[1] | | | | | | | | | | | |
|---|---|---|---|---|---|---|---|---|---|---|---|
| CROPS | | | GRASSES | | | | BROAD-LEAF WEEDS | | | | |
| Soybean | Cotton | Tomato | Foxtail Millet | Japanese Millet | Crabgrass | Wild Oats | Morning Glory | Mustard | Pigweed | Sesbania | Velvet Leaf |
| 0  1 | 0  5 | 0  10 | 0  4 | 0  2 | 0  8 | 0  3 | 0  3 | 0  10 | 0  9 | 0  8 | 0  10 |

[1]The left side for each column shows pre-emergence results; the right side for each column shows post-emergence results.

TABLE II

| LOWER DOSAGE POST-EMERGENCE HERBICIDE ACTIVITY | | | | | | | | | | | |
|---|---|---|---|---|---|---|---|---|---|---|---|
| CROPS | | | GRASSES | | | | BROAD-LEAF WEEDS | | | | |
| | Soybean | Cotton | Tomato | Foxtail Millet | Japanese Millet | Crabgrass | Wild Oats | Morning Glory | Mustard | Pigweed | Sesbania | Velvet Leaf |
| 2.5 Lb./Acre | 5 | 5 | 1 | 5 | 2 | 9 | 0 | 2 | 4 | 9 | 0 | 0 |
| 1.2 Lb./Acre | 0 | 3 | 0 | 3 | 1 | 6 | 0 | 1 | 3 | 8 | 0 | 0 |
| 0.6 Lb./Acre | 0 | 1 | 0 | 2 | 2 | 5 | 0 | 1 | 1 | 8 | 0 | 0 |

What is claimed is:

1. A compound of the formula

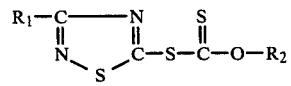

wherein $R_1$ is a $CCl_3$ or $CF_3$ group and $R_2$ is a lower alkyl group having 1 to 4 carbon atoms.

2. A compound of claim 1 having the formula

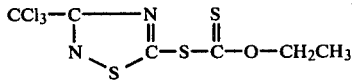

3. A method for controlling undesirable plant growth at a locus to be protected comprising applying to a locus a herbicidally effective amount of a compound as claimed in claim 1.

4. The method of claim 3 wherein said compound is

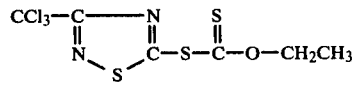

* * * * *